United States Patent [19]
Block et al.

[11] Patent Number: 6,090,403
[45] Date of Patent: Jul. 18, 2000

[54] INHALATION THERAPY DECONGESTANT WITH FORAMINOUS CARRIER

[75] Inventors: Leslie L. Block, Chaska; David J. W. Goon, Bloomington; David Rolf, Eden Prairie, all of Minn.

[73] Assignee: LecTec Corporation, Minnetonka, Minn.

[21] Appl. No.: 09/135,104

[22] Filed: Aug. 17, 1998

[51] Int. Cl.[7] .............................. A61L 15/16; A61F 13/02
[52] U.S. Cl. .......................... 424/447; 424/445; 424/448
[58] Field of Search ..................................... 424/443, 445, 424/447, 448

[56] References Cited

U.S. PATENT DOCUMENTS

| | | |
|---|---|---|
| 2,498,338 | 2/1950 | Martin . |
| 2,736,721 | 2/1956 | Dexter . |
| 2,814,601 | 11/1957 | Currie et al. . |
| 2,857,356 | 8/1958 | Goodwin, Jr. . |
| 3,627,851 | 12/1971 | Brady . |
| 3,645,835 | 2/1972 | Hodgson . |
| 3,772,247 | 11/1973 | Flannigan . |
| 4,427,737 | 1/1984 | Cilento et al. . |
| 4,655,767 | 4/1987 | Woodard et al. . |
| 4,675,009 | 6/1987 | Hymes . |
| 4,738,984 | 4/1988 | Parker ...................................... 514/473 |
| 4,826,683 | 5/1989 | Bates . |
| 4,867,150 | 9/1989 | Gilbert . |
| 4,927,631 | 5/1990 | Bates . |
| 4,951,657 | 8/1990 | Pfister et al. . |
| 4,970,240 | 11/1990 | Kielley . |
| 5,114,979 | 5/1992 | Kielley . |
| 5,232,702 | 8/1993 | Pfister et al. . |
| 5,288,492 | 2/1994 | Morris . |
| 5,322,689 | 6/1994 | Hughes et al. . |
| 5,459,157 | 10/1995 | Stroppolo et al. . |
| 5,478,565 | 12/1995 | Geria . |
| 5,536,263 | 7/1996 | Rolf et al. . |
| 5,562,908 | 10/1996 | Geria . |
| 5,681,577 | 10/1997 | Lech et al. . |

*Primary Examiner*—Carlos A. Azpuru
*Attorney, Agent, or Firm*—Schwegman, Lundberg, Woessner & Kluth P.A.

[57] ABSTRACT

A vaporizable decongestant is supported and stabilized on a flexible foraminous carrier composed typically of open-cell plastic foam, cloth or other fibrous material such as nonwoven fabric. The term "foraminous" herein is intended to refer to a substance or medium containing minute openings or perforated by many minute apertures. The decongestant is placed on the surfaces within the interstices and minute apertures or on fibers from which the foraminous carrier is formed. Vaporization of the inhalable decongestant is facilitated by providing the potential for greatly increasing its exposed surface area. Distributing the decongestant composition over the large, expanded surface within the foraminous carrier is beneficial in enhancing both the volatilization and evaporation of the decongestant agent. It also prolongs the useful life of the product. Once vaporized, the aromatic decongestant is available for natural inhalation through the nose or mouth to help relieve one or more of the symptoms of cough, colds, nasal or chest congestion and related symptoms. The foraminous carrier is preferably provided in the form of a patch or sheet that is bonded to the skin to serve as a supporting base for the active decongestant agent. The patch defining the carrier is typically adhesively bonded to the upper part of the body, e.g. on the face, neck or chest, in a location where the decongestant is liberated into the air and can be inhaled through the mouth or nose.

41 Claims, 5 Drawing Sheets

INHALATION THERAPY DECONGESTANT WITH FORAMINOUS CARRIER

FIELD OF THE INVENTION

This invention relates to inhalation therapy and more particularly to the inhalation of decongestants for the relief of nasal congestion, cough, colds or chest congestion.

BACKGROUND OF THE INVENTION

About $1.5 billion per year are estimated to be spent in over-the-counter cold medications in the United States. Inhalation therapy employed for the relief of bronchial spasms, bronchial asthma, bronchitis, the relief of cough, colds and nasal congestion as carried out at the present time requires a pressurized can for expelling a given quantity of an aerosol containing a therapeutic agent such as epinephrine. These containers are expensive, require the patient to follow instructions carefully, and must be administered according to a set schedule. Other vaporizers that are sometimes used are even more complex. Electric nebulizers and hot water vaporizers are examples. In addition to the expense, these products cannot be used out of doors or away from home. Consequently, they are unsuitable for use at the work place or while riding in a car. Because of these problems, decongestants such as camphor which are intended to be applied to the throat and chest are sometimes used to help relieve cough or cold symptoms. A decongestant of this type typically has a petrolatum base, giving it the consistency of petroleum jelly. One such product is sold under the trademark VICK'S VapoRub®. A similar topical aromatic composition is described in U.S. Pat. No. 5,322,689 but without a high level of petrolatum. Instead, a carboxylic acid copolymer is used. This composition, however, has the consistency of a fluid like the VICK'S product and is also applied topically. These products have significant drawbacks. Petroleum-based fluids are greasy and tend to be spread onto areas that are not intended. In addition, the fingers of the user must be dipped into the fluid product and, consequently, the product gets onto hands, on clothing, and can even be spread to areas where it can cause irritation, such as the nasal mucosa or the eyes. When applied by a healthcare worker, the smell of the decongestant can be carried away on hands and clothing. Moreover, because of the fluidity of such these products, they soon rub off onto the user's clothing and bed linens.

Another shortcoming of prior decongestants is the limitation on the rate of evaporation of the active aromatic substances. A large portion lies beneath the surface and is therefore not exposed to the air. The vaporization of this sub-surface material is therefore inhibited. One object of the present invention is to overcome this deficiency by finding a way to promote volatilization of active decongestant agents.

In view of these and other deficiencies of the prior art, it is one object of the present invention to provide a decongestant for alleviating one or more of the symptoms of nasal congestion, cough, colds or bronchial congestion but which is also comfortable to use, non-greasy and can be easily and quickly removed from the skin when no longer needed.

Another object is to provide an oral and nasal decongestant which readily evolves decongestant vapor that can be inhaled through the mouth or nose but will not spread out on the skin or be accidentally transferred to clothing.

Still another object of the invention is to provide an improved decongestant which readily diffuses into the air but still provides therapeutic effects that are long lasting.

A further object is to provide an improved decongestant and carrier for inhalation therapy which if desired can be structured to also provide analgesic effects through the skin.

These and other more detailed and specific objects of the present invention will be better understood by reference to the following figures and detailed description which illustrate by way of example of but a few of the various forms of the invention within the scope of the appended claims.

SUMMARY OF THE INVENTION

The present invention provides a decongestant, preferably an aromatic, vaporizable decongestant supported on a foraminous carrier composed typically of an open-cell plastic foam, perforated plastic film, cloth or other fibrous material such as nonwoven fabric. The term "foraminous" herein is intended to refer to a substance or medium containing minute openings or perforated by many minute apertures. To form such a product in accordance with the present invention, an inhalable decongestant is placed on surfaces within the interstices and minute apertures or on fibers of which the foraminous carrier is composed. In this way vaporization of the inhalable decongestant is facilitated by providing the potential for greatly increasing its exposed surface area. Thus, distributing the decongestant composition over the large, expanded surface within the foraminous carrier is beneficial in enhancing both the volatilization and evaporation of the decongestant agent. It also helps to prolong the useful life of the product. Once vaporized, the aromatic decongestant is available for natural inhalation through the nose or mouth to help relieve one or more of the symptoms of cough, colds, nasal or chest congestion and related symptoms. The foraminous carrier is preferably provided in the form of a patch or sheet that is bonded to the skin and acts as a supporting base for the active decongestant agent.

The patch defining the carrier is placed on the upper part of the body, typically on the face, neck or chest, in a location where the decongestant is liberated into the air and can be inhaled through the mouth or nose. The patch which serves as a carrier for the decongestant is bonded to the skin either through the provision of an adhesive on the lower surface of the patch or by means of a separate piece of pressure-sensitive adhesive tape or adhesive coating, either surrounding the carrier or applied along the edges of the lower surface of the carrier.

The decongestant can be applied to the foraminous carrier in various ways. For example, by spraying, roll-coating, dipping, knife-coating, or calendering. If desired, the decongestant agent can extend substantially through the entire thickness of the carrier sheet. It is preferred that the entire patch be non-occlusive, i.e. capable of allowing moisture from the skin to diffuse outwardly and escape through the upper surface of the patch. However, if desired, the foraminous carrier sheet can be provided as an upper layer of the patch which is bonded to a non-porous sheet material such as a sheet of plastic film having a separate layer of pressure-sensitive adhesive on its lower surface for bonding the patch to the skin. In this case, the patch as a whole is occlusive and as such will not allow moisture to escape from the skin.

A variety of well known therapeutic agents that have a decongestant or analgesic action can be employed. Examples include oil of wintergreen, menthol, thymol, camphor, oil of peppermint, eucalyptus oil, phenylephrine hydrochloride, pheniramine maleate, benzalkonium chloride, methyl salicylate, pseudoephedrine hydrochloride, oxymetazoline hydrochloride, xylometazoline hydrochloride, methazoline hydrochloride, epinephrine, spirits of turpentine, ephedra (ma huang), coltsfoot (*Tussilago farfara L.*), ginger (*Zingiber officinale*), naphazoline hydrochloride, and other decongestants known in the art. We have found that the turpentine, because of its volatility, appears to help co-evaporate other active decongestant agents. To prepare the patch, the decongestant, i.e. the therapeutic agent, is preferably dispersed in a vehicle to form an ointment that can either be hydrophilic or hydrophobic in nature. A typical hydrophilic vehicle preferably includes a thickener comprising a water-dispersible or water-swellable natural or synthetic polymer. The thickener raises the viscosity to a level that resists spreading and can, if desired, cause the ointment to set-up as an elastic solid. A hydrophilic ointment also contains water and a humectant such as a polyhydric alcohol. Typical hydrophobic vehicles comprise mineral oil or petroleum jelly, or a combination thereof, in which decongestant agents are dispersed or dissolved. Another hydrophobic vehicle comprises a pressure-sensitive adhesive matrix such as a dispersion of natural or synthetic rubber, an oleaginous plasticizer such as mineral oil, and a tackifying resin such as a terpene resin. Other adhesives can be used, such as vinyl emulsion adhesives, acrylic polymeric adhesives, vinyl acetate copolymers or silicone adhesives. Other medical adhesives which can be used will be apparent to those skilled in the art.

When the decongestant agents are mixed with the vehicle, an ointment is produced. The ointment is then stabilized by applying it to the greatly expanded surface area within the minute apertures and interstices between the fibrils, perforations and/or pores of the foraminous carrier. This, together with a thickening agent that can, if desired, be contained in the ointment, gives the ointment sufficient body, support and stability to hold it in place and prevent it from becoming smeared onto fingers, clothing, bed linens or onto other parts of the body where one or more of the decongestant agents could cause irritation, such as nasal mucosa or the eyes. In addition, the foraminous carrier supporting the decongestant enables all of the decongestant material to be easily and quickly removed when no longer needed with little or no residue left on the skin. In addition, by distributing the ointment over the extended surface of the foraminous carrier, more of the decongestant can be exposed to the air. The much greater exposed surface area facilitates evaporation of the decongestant, thus allowing more of the active agents it to be inhaled so as to improve the reduction of nasal or chest congestion and related cold and sinus symptoms.

DETAILED DESCRIPTION OF THE INVENTION

Figure 1:
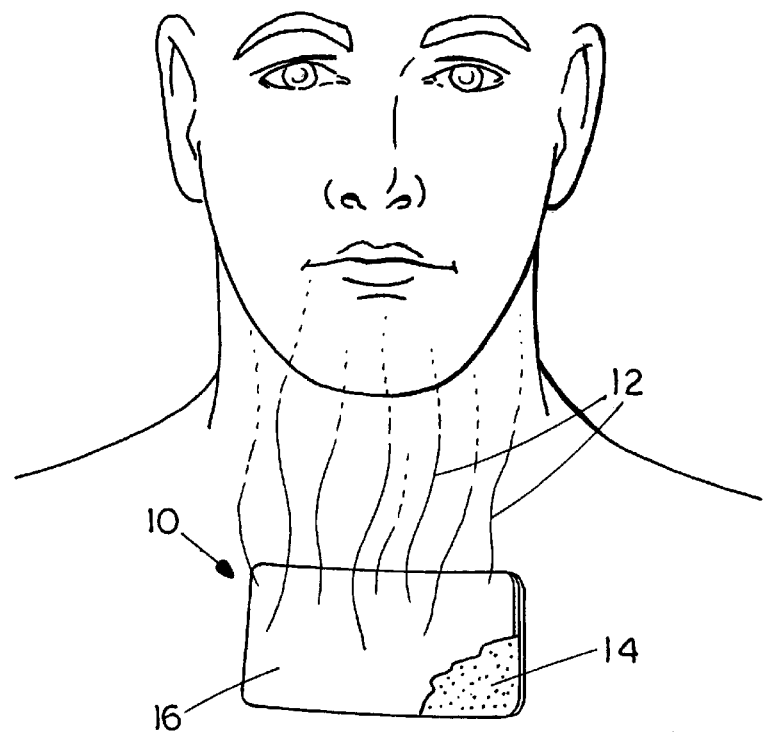
FIG. 1 is a perspective view showing the invention in use on the chest.
Figure 5:
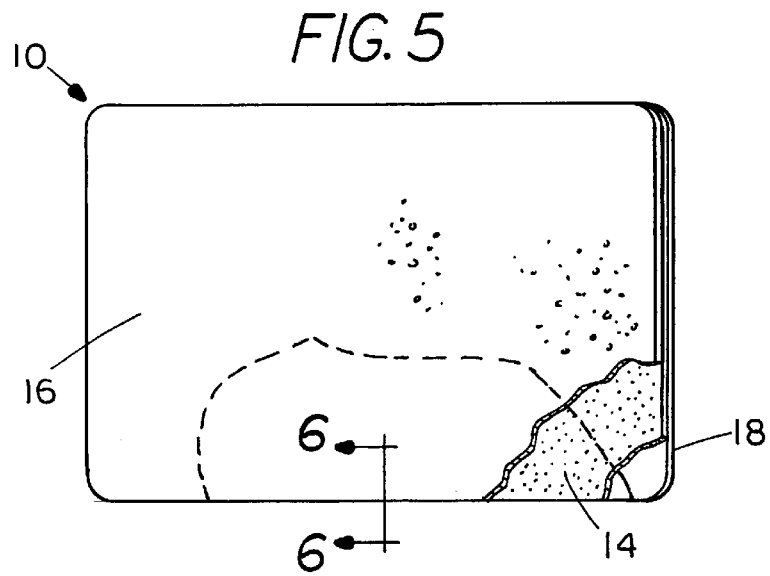
FIG. 5 is a greatly enlarged plan view of the invention.

Refer now to the figures in which the same numbers refer to corresponding parts in the several views, and particularly to FIGS. 1 and 5 which illustrate generally rectangular patch 10 that is applied to the upper chest area of a patient. The patch 10 includes an upper flexible foraminous decongestant-supporting carrier sheet 16 and is particularly advantageous for improving symptoms of chest congestion. The patch 10 provides for the evaporation of decongestant indicated diagrammatically at 12 which can then be inhaled by the patient through the nose or mouth. The warming of the patch 10 by the skin after the patch 10 has been applied helps to increase the rate of evaporation of the decongestant vapors 12. The patch 10 in this case is provided with an underlying layer of medical grade, non-irritating pressure-sensitive adhesive 14 of any suitable type known to those skilled in the art, for example as described in U.S. Pat. Nos. 5,536,263; 4,675,009; 2,498,338; 3,645,835; 4,427,737 and 4,867,150 which are incorporated herein by reference for bonding the patch to the skin. The lower surface of adhesive 14 is protected during shipment and storage by a removable liner sheet 18 (FIG. 5) that can comprise any suitable commercially available release paper or plastic film. Before use, the liner sheet 18 is removed to expose the lower surface of the pressure-sensitive adhesive 14. The patch 10 is then applied to the skin and is held in place by the pressure-sensitive adhesive, for example, on the upper chest area of the patient as shown in FIG. 1.

Overlying the pressure-sensitive adhesive 14 and bonded to it is the foraminous carrier 16 to which an ointment containing a decongestant is applied. If desired, the pressure-sensitive adhesive 14 can have the same composition as the ointment. In such a case, the pressure-sensitive adhesive 14 can also contain a therapeutic medicament comprising a decongestant and/or analgesic agent. It will then be possible for the decongestant or analgesic to be absorbed into the skin to provide a therapeutic effect by absorption into the underlying tissue to achieve localized relief for the symptoms of bronchial congestion. The invention is thus capable of providing a therapeutic effect in two ways simultaneously; namely, by dermal absorption into the skin as well as by inhalation of the decongestant vapors via the mouth or nose. In this way the invention can provide a dual therapeutic action. If the pressure-sensitive adhesive 14 is of a different composition from the ointment, for example an ordinary, non-irritating medical grade rubber-based adhesive, then the patch 10 will have but a single mode of operation; namely, the evolution of the aromatic decongestant vapor 12 for providing inhalation therapy. The patch 10 for use on the chest is typically about 3 inches long by 2 inches wide and has rounded corners. The foraminous carrier sheet typically has a thickness of about 3–8 mils and contains about 0.012 ounces per square inch of the decongestant-containing ointment. The foraminous carrier 16 is typically a flexible sheet of open-cell polyurethane foam, open-cell polyethylene foam, nonwoven fabric or cloth.

Figure 2:
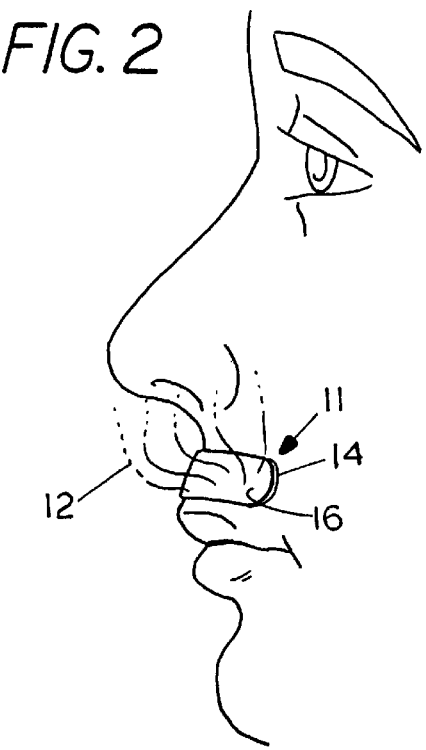
FIG. 2 is a perspective view showing use of the invention between the upper lip and nose.

Refer now to FIG. 2 which illustrates slightly curved patch 11 applied to the nasolabial area of a user just below the nose. The patch 10 is particularly advantageous for improving symptoms of nasal congestion or cough by providing for the evaporation of decongestant indicated diagrammatically at 12 into the air, which can then be inhaled by the patient through the nose. The patch 11 has a foraminous upper carrier layer 16 to which the decongestant-containing ointment is applied. The patch 10 also includes an underlying layer of non-irritating medical grade pressure-sensitive adhesive 14 of any suitable type known to those skilled in the art, for example as described above in connection with FIGS. 1 and 5. The adhesive 14 is protected during shipment and storage by a removable liner sheet (not shown) similar to 18 in FIG. 5 that can comprise any suitable commercially available release paper or plastic film. The pressure-sensitive adhesive 14 bonds the foraminous carrier 16 and the decongestant contained therein in place above the upper lip of the patient just below the nose as shown in FIG. 2.

The patch 11 for use between the upper lip and nose is typically about 2 inches long by ¾ inches wide and has rounded corners. The foraminous carrier sheet typically has a thickness of about 3–8 mils and contains about 0.012 ounces per square inch of the decongestant-containing ointment. The foraminous carrier 16 can comprise a sheet of open-cell foam plastic, such as a flexible sheet open-cell polyurethane foam, open-cell polyethylene foam, nonwoven fabric or cloth.

Figure 3:
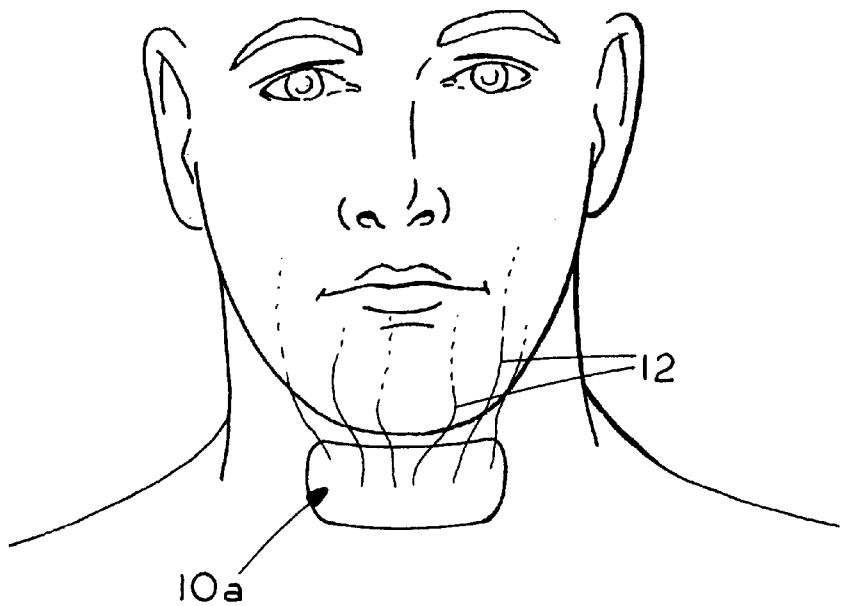
FIG. 3 is a perspective viewing showing use of the invention on the neck.
Figure 4:
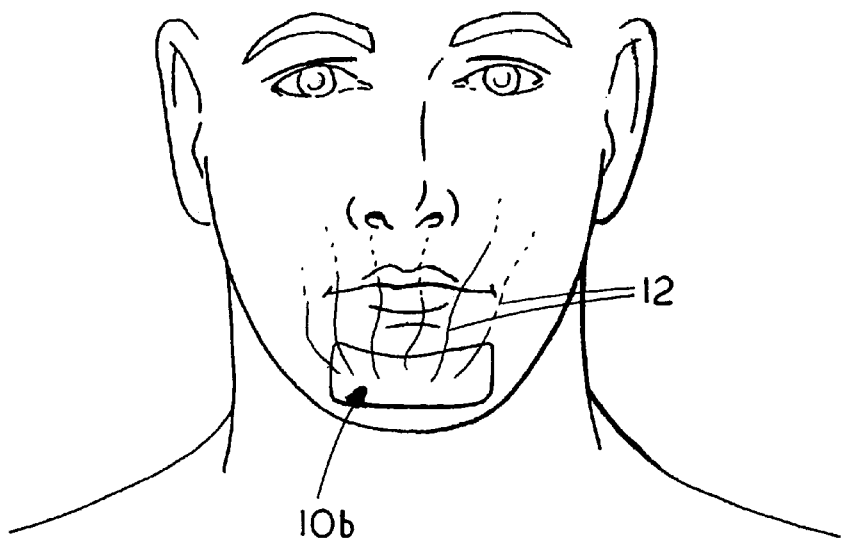
FIG. 4 is a perspective view showing the use of the invention on the chin.

Refer now to FIGS. 3 and 4 which illustrate generally rectangular patches 10a and 10b applied to the neck and chin, respectively. The patches 10a and 10b, which have the same construction described in connection with FIGS. 1 and 5 but are smaller, are especially useful for improving symptoms of head congestion. Both provide for the evaporation of decongestant into the air as indicated diagrammatically at 12. The vapor can then be inhaled by the patient through the nose or mouth. The construction of the patches 10a and 10b is the same as described above. The neck patch 10a of FIG. 3, however, has the decongestant ointment exposed on its lower surface and the ointment contains an adhesive material. Thus, the ointment provides an analgesic effect through dermal absorption, which is useful in relieving the symptoms of cough and itchy throat.

The patch 10a or 10b for use on the neck or chin is typically about 3 inches long by 2 inches wide and has rounded corners. The overall thickness can be about 5–22 mils and contains about 0.012 ounces per square inch of the decongestant-containing ointment. The foraminous carrier 16 can comprise a sheet of polyurethane foam, cloth or nonwoven fabric. The chin patch is especially advantageous for providing decongestant vapor for oral inhalation.

Figure 6:
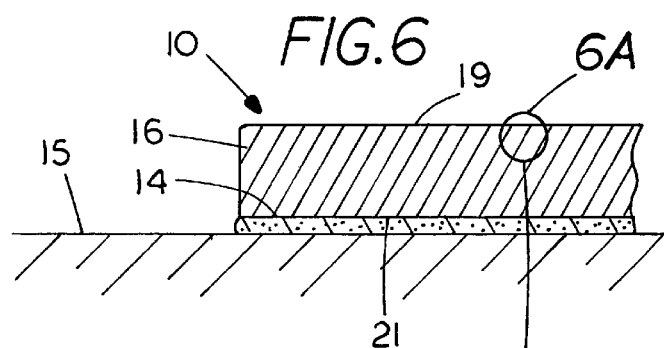
FIG. 6 is a cross-sectional view of the invention taken on line 6—6 of FIG. 5.
Figure 6A:
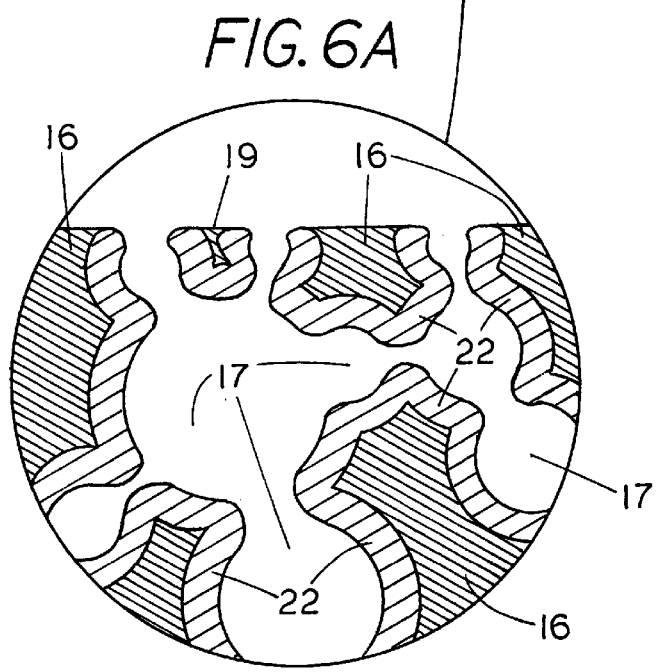
FIG. 6A is a microscopic cross-sectional view of FIG. 6.

Refer now to FIGS. 6 and 6A which illustrate cross-sectional views of the invention as it appears when applied to the skin 15 of a patient after removal of the liner sheet 18. The foraminous decongestant carrier 16 comprises an upper layer and the pressure-sensitive adhesive 14 comprises a lower layer. The foraminous carrier 16 contains openings or foramina 17 throughout which communicate between the upper and lower surfaces 19 and 21 of the foraminous carrier 16. This allows moisture from the skin 15 to escape through the patch 10. Applied to the surfaces lining the apertures and interstices 17 within the foraminous carrier 16 is a quantity of an ointment 22 containing the active aromatic decongestant agent. Support by the carrier 16 makes possible a greatly extended exposed surface due to the multiplicity of minute foramina 17 within the carrier 16. The increased extended surface area of the ointment within the carrier 16 makes possible much improved volatilization of the aromatic decongestant contained in the ointment, thereby enhancing the liberation of vapor into the air for inhalation therapy through the nose or mouth.

In the patch 10 of FIGS. 6 and 6A, the pressure-sensitive adhesive layer 14 has the same composition as the ointment 22 which contains both the active decongestant and a suitable adhesive and thickener such as a natural or synthetic polymeric adhesive or gum dispersed in the ointment 22.

Figure 7:
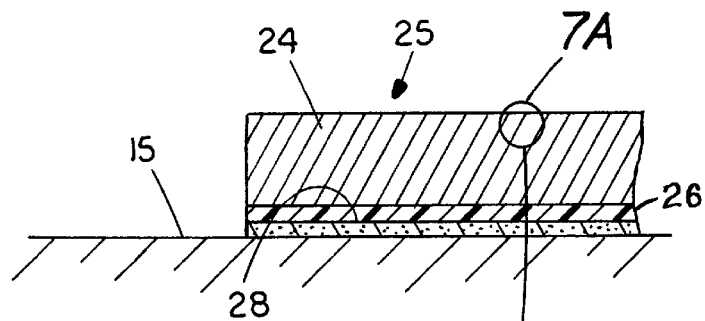
FIG. 7 is a cross-sectional view of another form of carrier.
Figure 7A:
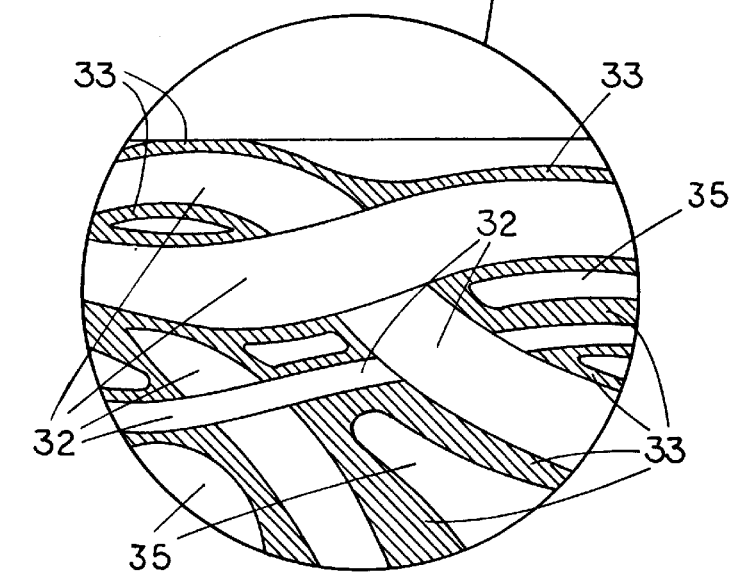
FIG. 7A is a microscopic view of FIG. 7 showing the active decongestant distributed on the extended surface of the foraminous carrier.

Refer now to FIGS. 7 and 7A which illustrate a modified form of the invention. In FIG. 7, a foraminous carrier sheet designated 24 comprises a fibrous sheet formed from non-woven cotton fabric containing microscopic fibers 32 (FIG. 7A) which are bonded together at their points of contact. A typical foraminous carrier is a flexible sheet about 5 mils thick. Applied within the foramina 35 to the surfaces of the fibers 32 is a decongestant ointment 33. Bonded to the lower surface of the foraminous carrier 24 by the ointment is a barrier such as a sheet of plastic film, e.g. 2 mil. polyester film 26. Applied as a coating on the lower surface of the polyester film 26 is a layer of commercially available medical grade non-irritating pressure-sensitive adhesive 28 that bonds the patch 25 to the skin 30. The foraminous carrier layer 24 comprises a fibrous mass of intersecting fibers 32 (FIG. 7A) to which the ointment 33 is applied. The microscopic fibers 32 provide an extremely high surface area. This can give the applied ointment 33 containing the active decongestant agent a greatly extended surface area which, as already noted, helps to volatilize the decongestant thus making it more available for inhalation therapy so as to provide greater effectiveness in the relief of the symptoms of cough, colds, nasal congestion or chest congestion. At the same time, the foraminous carrier 24 stabilizes the ointment by holding it in place and keeping the ointment it from spreading onto other parts of the body, the clothing, bed linens, etc. In this embodiment, the ointment 33 contains a thickener that helps the ointment set or gel once applied to the foraminous carrier 24. For this purpose, we employ a high molecular weight natural or synthetic polymer and optionally a polymeric adhesive as a part of the ointment. Accordingly, the upper portion of the patch 25 can be thought of as a stabilized ointment containing a vaporizable decongestant that is spread over an extended surface of the solid but flexible foraminous carrier 24.

The form of the invention shown in FIGS. 7 and 7A has an important advantage since the decongestant contained in the foraminous carrier 24 does not contact the skin. This benefits some people, particularly those with sensitive skin and children, who sometimes complain about the tingling or burning sensation that is noticed when certain decongestants are placed in direct contact with the skin.

Figure 8:
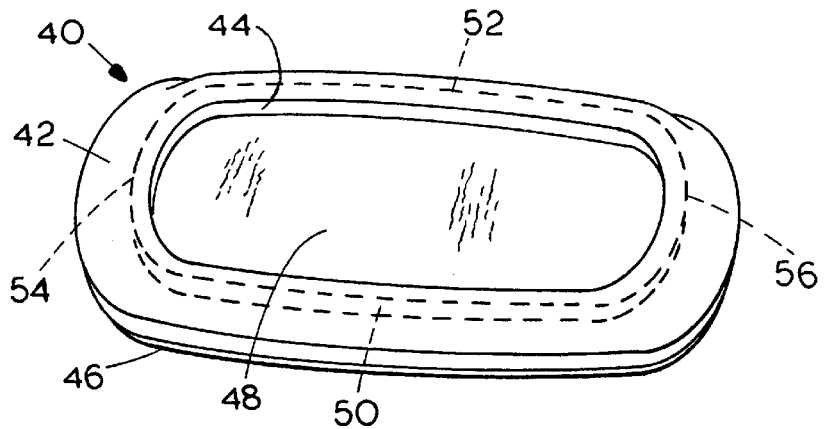
FIG. 8 is a perspective view of the invention in which medical adhesive tape is used to bond the carrier to the skin.

Refer now to FIG. 8 which illustrates a decongestant patch 40 in accordance with the invention that is held in place on the skin by means of a sheet of medical grade adhesive tape 42 having an opening 44 cut in its center. The adhesive tape 42 is elongated and has rounded corners. The adhesive tape 42 can be any suitable commercially available medical adhesive tape having an adhesive layer 46 on its lower surface for bonding the patch 40 to the skin and for bonding the adhesive tape 42 to the edge of a flexible foraminous carrier sheet 48 which typically comprises a sheet of plastic foam, fibrous material such as woven or nonwoven plastic or gauze saturated with an aromatic decongestant. The foraminous carrier 48 has side edges 50, 52 and end edges 54, 56 which are all bonded in place by the inner edge of the adhesive tape 42 adjacent the opening 44. It will be understood that the foraminous carrier sheet 48 itself has no adhesive and depends entirely upon the adhesive tape 42 to hold it in place on the skin. The patch 40 can be made in any suitable size and positioned conveniently on the skin wherever desired so that the decongestant vapors when given off can be inhaled through the mouth or nose during normal respiration.

Figure 9:
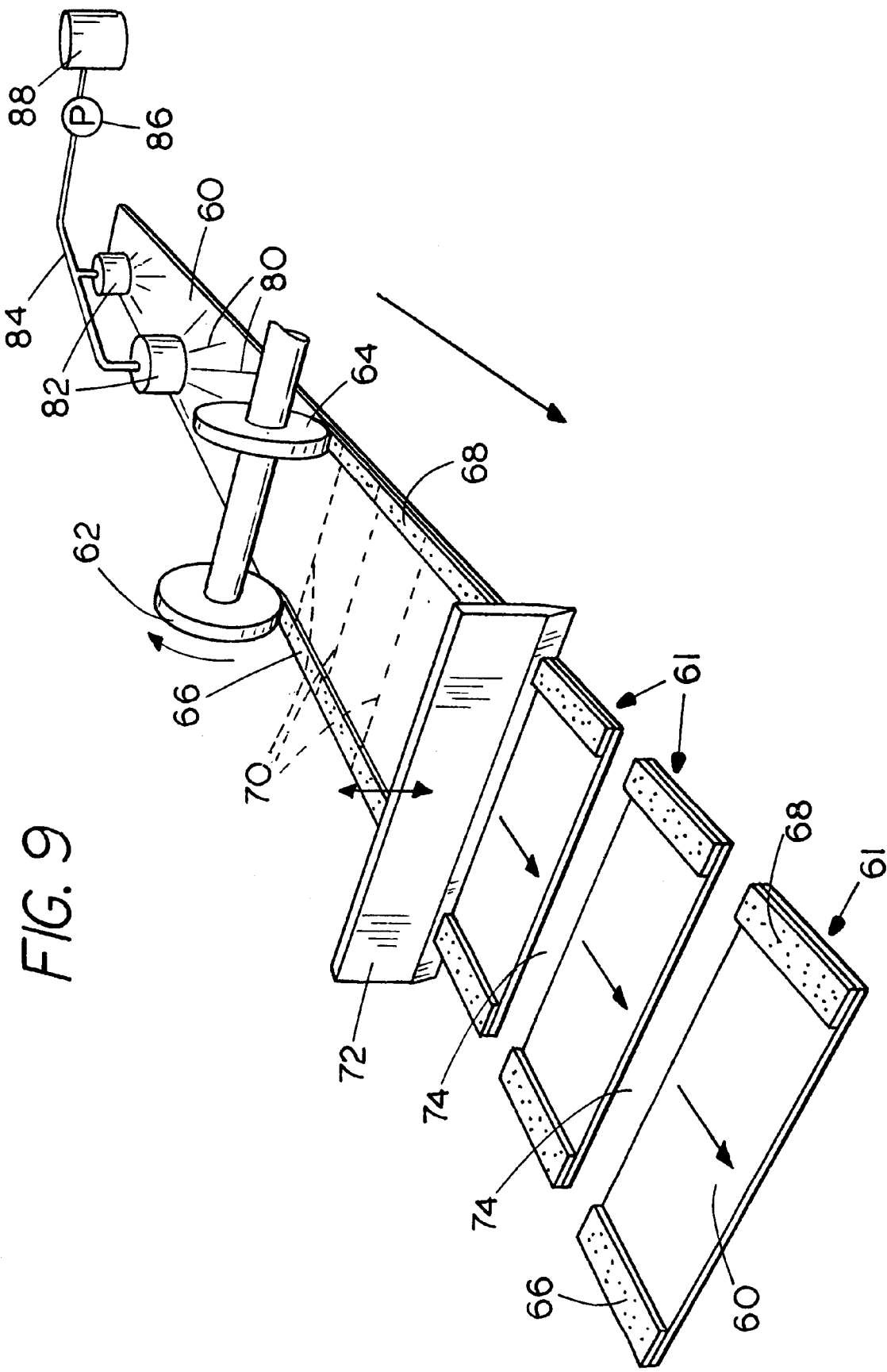
FIG. 9 is a perspective view showing the application of adhesive along the edges of decongestant patches embodying the invention.

Refer now to FIG. 9 which illustrates the application of adhesive bands on opposed edges of the invention for securing the flexible foraminous carrier to the skin. In FIG. 9, the foraminous carrier 60 which comprises a strip of fabric passes from right to left in the figure beneath adhesive applicator rolls 62, 64 which rotate in a given feed direction to apply strips of adhesive 66, 68 along parallel opposed edges of the carrier 60. Pressure-sensitive adhesive (not shown) is applied continually to the rolls 62, 64 to keep the surface of the rolls 62, 64 coated with adhesive. The foraminous carrier sheet 60 is periodically cut transversely in any suitable manner along separation lines indicated at 70 by a cutter such as a reciprocating blade 72 which severs the carrier sheet 60 transversely at spaced apart locations indicated at 74 to provide finished patches 61 with pressure-sensitive adhesive strips 66, 68 along opposed edges. The carrier sheet 60 can be of any of the compositions described above. Prior to passing beneath rolls 62, 64, a vaporizable decongestant agent 80 of a suitable composition is applied as a spray by means of spray heads 82 to which the decongestant is pumped under pressure through a feed line 84 by means of pump 86 from supply tank 88. The spray of decongestant material 80 impinges upon the carrier sheet 60 so as to coat the fibers that line the openings or foramina within the foraminous structure of the carrier 60. If desired, heat can be applied to the sheet 60 to drive off excess moisture and to help thicken the decongestant 80 that has been applied by the spray heads 82. The decongestant is then supported and stabilized by the foraminous structure of the carrier 60 and, if desired, by a thickening agent contained in the decongestant as described above. The patches 61 are used in the same manner as described above and can be made in any convenient size. In this case the decongestant spray 80 itself contains no adhesive since the patches 61 will be adequately bonded to the skin by means of the pressure-sensitive adhesive strips 66, 68.

For various applications, the patches can measure from about 2 inches by 3 inches to about 4 inches by 5 inches, or larger, for application to the chin, neck or chest. When the patch is applied to the nasolabial area just beneath the nose, it can be about 2¾ inches long by ⅜ inches wide with a slight concave upper edge if desired. The patches can be made in other sizes and shapes to fit the portion of the body to which they are applied.

The ointment is prepared by mixing together a vehicle preferably containing a polymeric thickener, either with water or non-polar solvent as the case may be, and a pre-mix containing the active decongestant agent. If the ointment is formed with an aqueous base, a preferred thickener comprises a hydrophilic polymer that is either soluble in water or will swell in contact with water. A humectant such as a polyhydric alcohol is also advantageously employed. The method used for mixing the ointment can be similar to the method used for preparing the medication-containing reservoir described in U.S. Pat. No. 5,536,263 which is incorporated herein by reference.

One preferred form of ointment contains the following: about 0.1% to about 10% camphor; about 0.5% to about 5% menthol; about 0.1% to about 5% eucalyptus oil; about 0.5% to about 10% spirits of turpentine; about 10% to about 60% of a humectant of which a polyhydric alcohol such as glycerin or propylene glycol are examples; and a thickener comprising a natural or synthetic polymeric gum such as karaya or polyacrylamide is provided in the amount of about 5% to about 50%. The active decongestant is preferably prepared as a pre-mix by blending ingredients together in a suitable mixer and then admixing the pre-mix to the ingredients present in the vehicle. All quantities herein are presented as percent by weight unless otherwise specified.

A variety of other natural or synthetic gel-forming polymers can be used as a thickener in place of karaya or polyacrylamide. These include gum acacia, locust bean gum, guar gum, modified guar gum, maltodextrin, carboxymethyl cellulose, carboxypropyl cellulose, and polyacrylic acid. Optionally, a water dispersible adhesive is provided, such as a carboxylic acid polymer, e.g. Carbotac™ 26222 or 26171 by the B. F. Goodrich Company of Cleveland, Ohio, in the amount of about 0.5% to about 30%. The adhesive, however, can be any suitable non-irritating medical grade adhesive including adhesives such as acrylate emulsion adhesive, acrylic ester copolymer adhesives, vinyl acetate resins, and copolymers of vinyl acetate and dioctyl maleate and the like. Other pressure-sensitive adhesives can be employed such as silicone pressure-sensitive adhesives prepared as described in U.S. Pat. Nos. 3,627,851; 3,772,247; 2,736,721 and 2,814,601 each of which is incorporated herein by reference. Still other pressure-sensitive adhesives that can be used are described in U.S. Pat. No. 2,857,356 which is also incorporated herein by reference. Additional adhesives which can be used are described as adhesives for transdermal delivery devices in U.S. Pat. Nos. 4,951,657; 4,655,767 and 5,232,702 which are all incorporated herein by reference.

One preferred ointment comprises about 6% camphor; about 3% menthol; about 1% eucalyptus oil; about 4% spirits of turpentine; about 44% glycerin; about 1% aloe vera; a thickener comprising about 34% karaya gum; and about 7% of a water-borne latex adhesive such as a carboxylic acid polymeric adhesive, e.g. 2 parts Carbotac™ 26222 and 1 part Carbotac™ 26171. The ointment can be applied to the foraminous carrier either by roll-coating or by knife-coating without dilution or, if applied by spraying or dipping, it can be diluted with an equal amount of water. After being applied, the ointment is then preferably heated, e.g. to between about 120° F. and 150° F. to help drive off excess moisture and to assist in setting the structure of the ointment within the minute foramina of the carrier. This distribution of the decongestant promotes volatilization and evaporation of the active decongestant agent and helps to keep the ointment where it is placed. It also allows it to be cleanly removed from the skin when no longer needed.

The invention has been well received by users because it prevents clothes and fingers from becoming smeared with ointment, while holding the ointment in place where the decongestant vapors will be readily available for inhalation. The invention is also capable of distributing the ointment over the relatively large extended surface of the foraminous carrier to aid in promoting the transfer of the decongestant from the solid state to the vapor state. The invention also enables the decongestant vapor to be reliably evolved over a relatively long period of time, e.g. up to eight or more hours, and was therefore adjudged long-lasting by the average user. In addition, the invention enables the decongestant to act in a dual capacity; namely, both as a vaporous inhalant and also as an analgesic through dermal absorption into the capillaries beneath the skin surface. The decongestant-containing patches have proved effective in the temporary relief of coughs due to colds, minor throat and bronchial irritation, and temporarily suppresses cough occurring with a cold. When used on the chest, the invention temporarily relieves cough due to colds, minor throat and bronchial irritation and temporarily suppresses cough occurring with a cold. On the chest it can also act as a topical analgesic to relieve minor aches and pains in the chest area via dermal absorption through the skin. The decongestant patches of the present invention are comfortable, non-greasy and easy to apply with little, if any, traces of greasy material being left after removal or transferred to the fingers, clothes or bed linens. The decongestant agents are readily vaporized, and the patch as a whole can be made non-occlusive so as to eliminate the possibility of perspiration becoming trapped beneath the patch. The patches can be made so as to keep the decongestant agent away from the skin to prevent possible irritation. The invention also helps people without cold symptoms to sleep better by making it possible for one to breathe easily through the nose throughout the entire night. The invention is therefore also a sleep aid. Finally, the inhalable decongestants do not appear to interact with other medications that may be taken by the patient.

The finished patches are preferably packaged in envelopes or boxes with instructions to apply them to the upper part of the body; namely, the nasolabial area, the chest, the chin, and the throat.

Many variations of the present invention within the scope of the appended claims will be apparent to those skilled in the art once the principles described herein are understood.

What is claimed is:

1. A skin patch for the relief of the symptoms of cough, colds, nasal congestion or chest congestion, comprising, symptomatic cold reliever supported upon a non-occlusive flexible foraminous carrier and means operatively associated with the carrier for securing the carrier to the skin surface to enable said symptomatic cold reliever to be available for natural inhalation during respiration through the mouth or nose;

wherein the skin patch is free of a 5-substituted furan methyl ketone.

2. The skin patch of claim 1 wherein the symptomatic cold reliever is an ointment containing an active agent selected from the group consisting of oil of wintergreen, menthol, thymol, camphor, oil of peppermint, eucalyptus oil, phenylephrine hydrochloride, pheniramine maleate, benzalkonium chloride, methyl salicylate, pseudoephedrine hydrochloride, oxymetazoline hydrochloride, xylometazoline hydrochloride, methazoline hydrochloride, epinephrine, spirits of turpentine, ephedra (ma huang), coltsfoot (*Tussilago farfara L.*), ginger (*Zingiber officinale*), and naphazoline hydrochloride.

3. The skin patch of claim 1 wherein the symptomatic cold reliever is dispersed in an ointment including as a thickener a natural or synthetic gel-forming polymer comprising a member selected from the group consisting of gum karaya, gum acacia, locust bean gum, guar gum, modified guar gum, maltodextrin, carboxymethyl cellulose, carboxypropyl cellulose, polyacrylamide, and polyacrylic acid.

4. The skin patch of claim 1 wherein the symptomatic cold reliever is dispersed in a vehicle that includes a resin emulsion adhesive.

5. The skin patch of claim 1 wherein said means comprises an adhesive selected from the group consisting of acrylate emulsion adhesive, an acrylic ester copolymer, a vinyl acetate resin, a copolymer of vinyl acetate and dioctyl maleate, silicone adhesive, natural or synthetic rubber, a petroleum derivative, and a resin.

6. The skin patch of claim 3 wherein the symptomatic cold reliever is dispersed in a vehicle which includes a humectant comprising a polyhydric alcohol.

7. A skin patch, comprising, a patch body including a flexible foraminous carrier sheet having a multiplicity of minute foramina extending therethrough to provide an extended surface, an ointment containing a symptomatic cold reliever, said ointment being distributed upon the extended surface of the foramina within the carrier for supporting and stabilizing the ointment and to promote volatilization and evaporation of the symptomatic cold reliever for inhalation through the nose or mouth to relieve of one or more of the symptoms of cough, cold, nasal congestion, or chest congestion.

8. The skin patch of claim 7 wherein a pressure-sensitive adhesive is exposed on the lower surface of said skin patch for bonding the patch to the skin of a patient.

9. The skin patch of claim 7 wherein said ointment contains a symptomatic cold reliever selected from the group consisting of oil of wintergreen, menthol, thymol, camphor, oil of peppermint, eucalyptus oil, phenylephrine hydrochloride, pheniramine maleate, benzalkonium chloride, methyl salicylate, pseudoephedrine hydrochloride, oxymetazoline hydrochloride, xylometazoline hydrochloride, methazoline hydrochloride, epinephrine, spirits of turpentine, ephedra (ma huang), coltsfoot (*Tussilago farfara L.*), ginger (*Zingiber officinale*), and naphazoline hydrochloride.

10. The skin patch of claim 7 wherein the ointment includes a thickener comprising a natural or synthetic gel-forming polymer selected from the group consisting of gum karaya, gum acacia, locust bean gum, guar gum, modified guar gum, maltodextrin, carboxymethyl cellulose, carboxypropyl cellulose, polyacrylamide, and polyacrylic acid.

11. The skin patch of claim 7 wherein the ointment includes a resin emulsion adhesive.

12. The skin patch of claim 7 wherein the ointment includes an emulsion adhesive comprising a member selected from the group consisting of acrylate emulsion adhesive, an acrylic ester copolymer, a vinyl acetate resin, a copolymer of vinyl acetate and dioctyl maleate, and silicone adhesive.

13. The skin patch of claim 10 wherein the ointment includes a humectant comprising a polyhydric alcohol.

14. A skin patch, comprising, a flexible laminate for being bonded to the skin of a patient, said laminate including a vehicle containing a symptomatic cold reliever on at least an upper portion thereof, a carrier for the vehicle comprising a sheet of flexible foraminous material to support the vehicle, and a pressure-sensitive adhesive exposed on a lower surface of said patch for bonding the patch to the skin of a patient wherein the skin patch is free of a 5-substituted furan methyl ketone.

15. The skin patch of claim 14 wherein the pressure-sensitive adhesive is a layer of adhesive material applied to a lower surface of said skin patch for bonding the patch to the skin of a patient.

16. The skin patch of claim 14 wherein the symptomatic cold reliever comprises an active agent selected from the group consisting of oil of wintergreen, menthol, thymol, camphor, oil of peppermint, eucalyptus oil, phenylephrine hydrochloride, pheniramine maleate, benzalkonium chloride, methyl salicylate, pseudoephedrine hydrochloride, oxymetazoline hydrochloride, xylometazoline hydrochloride, methazoline hydrochloride, epinephrine, spirits of turpentine, ephedra (ma huang), coltsfoot (*Tussilago farfara L.*), ginger (*Zingiber officinale*), and naphazoline hydrochloride.

17. The skin patch of claim 14 wherein the symptomatic cold reliever is dispersed in a vehicle including a thickener comprising a natural or synthetic gel-forming polymer selected from the group consisting of gum karaya, gum acacia, locust bean gum, guar gum, modified guar gum, maltodextrin, carboxymethyl cellulose, carboxypropyl cellulose, polyacrylamide, polyacrylic acid, a natural or synthetic rubber, a petroleum derivative, and a resin.

18. The skin patch of claim 14 wherein the symptomatic cold reliever is dispersed in a vehicle that includes a resin emulsion adhesive.

19. The skin patch of claim 14 wherein the symptomatic cold reliever is dispersed in a vehicle including an emulsion adhesive comprising a member selected from the group consisting of acrylate emulsion adhesive, an acrylic ester copolymer, a vinyl acetate resin, a copolymer of vinyl acetate and dioctyl maleate, and silicone adhesive.

20. The skin patch of claim 17 wherein the symptomatic cold reliever is contained in a vehicle that includes a humectant comprising a polyhydric alcohol.

21. A method of reducing or alleviating one or more of the symptoms of cough due to colds, minor throat and bronchial imtation, nasal or chest congestion, comprising,
providing a flexible foraminous carrier,
supporting a symptomatic cold reliever upon the foraminous carrier, and
providing instructions for bonding the foraminous carrier to the skin surface in sufficient proximity to the nose or mouth to enable the symptomatic cold reliever to be available for natural inhalation during respiration through the nose or mouth wherein the skin patch is free of a 5-substained furan methyl ketone.

22. The method of claim 21 wherein the symptomatic cold reliever is an ointment-containing an active agent selected from the group consisting of oil of wintergreen, menthol, thymol, camphor, oil of peppermint, eucalyptus oil, phenylephrine hydrochloride, pheniramine maleate, benzalkonium chloride, methyl salicylate, pseudoephedrine hydrochloride, oxymetazoline hydrochloride, xylometazoline hydrochloride, methazoline hydrochloride, epinephrine, spirits of turpentine, ephedra (ma huang), coltsfoot (*Tussilago farfara L.*), ginger (*Zingiber officinale*), and naphazoline hydrochloride.

23. The method of claim 21 wherein the symptomatic cold reliever is dispersed in a vehicle which includes a thickener comprising a natural or synthetic polymer.

24. The method of claim 23 wherein the polymer comprises a member selected from the group consisting of karaya gum, gum acacia, locust bean gum, guar gum, modified guar gum, maltodextrin, carboxymethyl cellulose, carboxypropyl cellulose, polyacrylamide, and polyacrylic acid.

25. The method of claim 21 wherein the foraminous carrier is bonded to the skin by a non-irritating medical grade, pressure-sensitive adhesive connected to the carrier.

26. The method of claim 25 wherein the pressure-sensitive adhesive comprises a member selected from the group consisting of acrylate emulsion adhesive, an acrylic ester copolymer, a vinyl acetate resin, a copolymer of vinyl acetate and dioctyl maleate, silicone adhesive, natural or synthetic rubber, a petroleum derivative, and a resin.

27. The method of claim 21 wherein the instructions direct one to apply the foraminous carrier to the nasolabial area beneath the nose.

28. The method of claim 21 wherein the instructions direct one to apply the foraminous carrier to the chin.

29. The method of claim 21 wherein the instructions direct one to apply the foraminous carrier to the chest.

30. The method of claim 21 wherein the instructions direct one to apply the foraminous carrier to the throat.

31. The skin patch of claim 7 wherein the skin patch provides a dual therapeutic action including vapor inhalation of the symptomatic cold reliever and dermal absorption of said symptomatic cold reliever into the skin and the underlying tissue.

32. The skin patch of claim 1 wherein the foraminous carrier is a perforated plastic film.

33. The skin patch of claim 31 wherein the symptomatic cold reliever is absorbed into the skin and underlying tissue.

34. The skin patch of claim 31 wherein the ointment contains an analgesic and the symptomatic cold reliever absorbed into the skin and underlying tissue is said analgesic.

35. A skin patch for the relief of the symptoms of cough, colds, nasal congestion or chest congestion, comprising,
a symptomatic cold reliever supported upon a flexible foraminous carrier and means operatively associated with the carrier for securing the carrier to the skin surface to enable the symptomatic cold reliever to be available for natural inhalation during respiration through the mouth or nose;
wherein the symptomatic cold reliever is dispersed in a vehicle that includes a resin emulsion adhesive wherein the skin patch is free of a 5-substituted furan methyl ketone.

36. A skin patch for the relief of the symptoms of cough, colds, nasal congestion or chest congestion, comprising,
a symptomatic cold reliever supported upon a flexible foraminous carrier and means operatively associated with the carrier for securing the carrier to the skin surface to enable the symptomatic cold reliever to be available for natural inhalation during respiration through the mouth or nose;
wherein the means comprises an adhesive selected from the group consisting of acrylate emulsion adhesive, an acrylic ester copolymer, a vinyl acetate resin, a copolymer of vinyl acetate and dioctyl maleate, silicone adhesive, natural or synthetic rubber, a petroleum derivative, and a resin wherein the skin patch is free of a 5-substituted furan methyl ketone.

37. A skin patch for the relief of the symptoms of cough, colds, nasal congestion or chest congestion, comprising,
a symptomatic cold reliever supported upon a flexible foraminous carrier and means operatively associated with the carrier for securing the carrier to the skin surface to enable the symptomatic cold reliever to be available for natural inhalation during respiration through the mouth or nose;
wherein the symptomatic cold reliever is dispersed in an ointment including as a thickener a natural or synthetic gel-forming polymer comprising a member selected from the group consisting of gum karaya, gum acacia, locust bean gum, guar gum, modified guar gum, maltodextrin, carboxymethyl cellulose, carboxypropyl cellulose, polyacrylamide, and polyacrylic acid; and
wherein the symptomatic cold reliever is dispersed in a vehicle which includes a humectant comprising a polyhydric alcohol wherein the skin patch is free of a 5-substituted furan methyl ketone.

38. The skin patch of claim 1 wherein the symptomatic cold reliever is a cough suppressant.

39. The skin patch of claim 38 wherein the cough suppressant is a topical antitussive.

40. The skin patch of claim 39 wherein the topical antitussive is camphor or menthol.

41. The skin patch of claim 7 wherein the skin patch provides a therapeutic action including vapor inhalation of the symptomatic cold reliever.

* * * * *